United States Patent [19]

Kohn et al.

[11] 4,272,449
[45] Jun. 9, 1981

[54] PHENOXY IMIDATES

[75] Inventors: Gustave K. Kohn; Ted A. Baer, both of Palo Alto, Calif.

[73] Assignee: Zoecon Corporation, Palo Alto, Calif.

[21] Appl. No.: 151,490

[22] Filed: May 19, 1980

Related U.S. Application Data

[62] Division of Ser. No. 102,050, Dec. 10, 1979.

[51] Int. Cl.³ .......................................... C07C 119/20
[52] U.S. Cl. ............................................... 260/453.99
[58] Field of Search .................. 260/453 RW, 453.99

[56] References Cited

U.S. PATENT DOCUMENTS 3,962,303  6/1976  Meier et al. ................ 260/453 RW

*Primary Examiner*—John M. Ford
*Assistant Examiner*—Robert C. Whittenbaugh
*Attorney, Agent, or Firm*—Donald W. Erickson; Thomas T. Gordon

[57] ABSTRACT

Novel imidates, intermediates therefor, synthesis thereof and the use of said imidates for the control of pests.

15 Claims, No Drawings

PHENOXY IMIDATES

This is a division of application Ser. No. 102,050, filed Dec. 10, 1979.

This invention relates to novel imidates, intermediates therefor, synthesis thereof and the use of said imidates for the control of pests.

The compounds of the present invention are represented by the following formula (A):

wherein,

R is hydrogen, lower alkyl, phenyl or substituted phenyl;

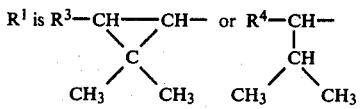

where $R^3$ is lower alkyl, lower haloalkyl, lower alkenyl or lower haloalkenyl and $R^4$ is the group

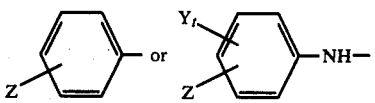

in which t is zero, one, two, three or four; Y is independently selected from hydrogen, lower alkyl, lower fluoroalkyl, lower alkoxy, lower alkylthio, lower alkylcarbonyl, lower alkoxycarbonyl, halogen, and lower fluoroalkylthio; and Z is independently selected from the values of Y, cycloalkyl, and lower fluoroalkoxy; or Y and Z form a methylenedioxy group; and

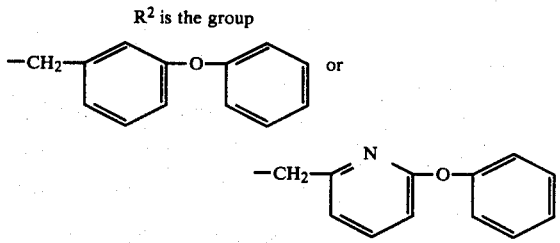

The compounds of the present invention represented by formula (A) are useful agents for the control of pests such as insects and acarids.

In the description hereinafter and the appended claims, each of R through $R^4$, t, Y and Z is defined hereinabove, unless otherwise specified.

The compounds of formula (A) can be synthesized as outlined below.

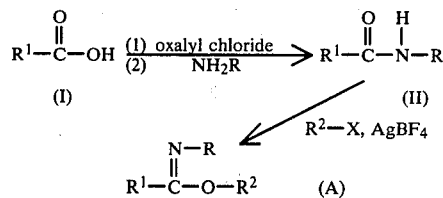

In the general practice of the above synthesis, the acid chloride made from reaction of the carboxylic acid (I) and oxalyl chloride, is reacted with an amine $NH_2$—R. The resulting amide (II) is then reacted with a halide $R^2$—X (X is bromo or chloro) in the presence of silver tetrafluoroborate to form the imidate (A).

An alternate method of synthesis of the compounds of the present invention, when R is H, can be illustrated as follows (R' is lower alkyl):

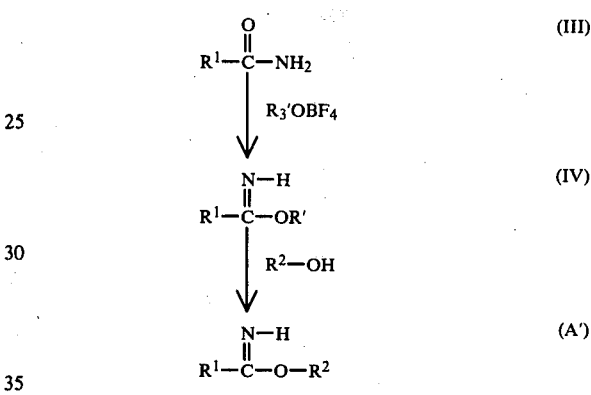

In the above general synthesis, the amide (III) is treated with a trialkyloxonium tetrafluoroborate to form the imidate (IV). Upon transesterification, compound IV is converted to the desired imidate (A').

The imidates of formula (IV) wherein $R^1$ is a phenylamino group can be synthesized also by treatment of a nitrile (V) with HCl or other strong acid in an alcohol R'—OH.

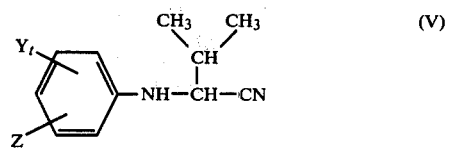

The following terms, wherever used in the description herein and the appended claims, have the meaming defined below, unless otherwise specified hereinafter.

The term "lower alkyl" refers to an alkyl group, straight or branched, having a chain length of one to six carbon atoms. The term "lower haloalkyl" refers to an alkyl group substituted with one to three halogen atoms such as chloromethyl, fluoromethyl, trifluoromethyl, 2,2,2-trifluoroethyl, 6-chlorohexyl, 2-fluoroethyl, and the like. The term "lower fluoroalkyl" refers to an alkyl group substituted with one to three fluorine atoms. The term "lower alkoxy" refers to an alkoxy group, straight or branched, having a chain length of one to eight carbon atoms. The term "lower alkylthio" refers to an alkylthio group, straight or branched, having a chain length of one to eight carbon atoms.

The term "cycloalkyl" refers to a cycloalkyl group of three to eight cyclic carbon atoms.

The term "lower alkenyl" refers to an ethylenically unsaturated hydrocarbon group, straight or branched, having a chain length of two to eight carbon atoms and one or two ethylenic bonds such as vinyl, allyl, 3-butenyl, 2-hexenyl, i-propenyl, 2,4-hexadienyl, and the like. The term "lower haloalkenyl" refers to a lower alkenyl group substituted with one to three halogen atoms.

The term "substituted phenyl" refers to a phenyl group substituted at one, two or three of the ring carbon atoms with a group selected from lower alkyl, lower fluoroalkyl, lower alkoxy, lower alkenyl, lower haloalkenyl, lower alkenyloxy, halogen, nitro, cyano, lower alkylthio, and the like.

The term "lower fluoroalkoxy" refers to a lower alkoxy group substituted with one to three fluorine atoms.

The term "lower acyloxy" refers to a lower organic acyloxy group of one to six carbon atoms, such as acetoxy.

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

The compounds of the present invention of formula A are useful pest control agents, particularly for the control of insects and acarids. In the use of the compounds of formula A for combating insects and acarids for the protection of agricultural crops, for example, soybeans, cotton, alfalfa, etc., a compound of formula A, or mixtures thereof, together with a carrier is applied to the locus in a pesticidally effective amount. The carrier can be liquid or solid and include adjuvants such as wetting agents, dispersing agents and other surface active agents. The compounds of formula A can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketone, and the like. The amount of a compound of formula A in the formulation can vary widely, generally within th range of about 0.01 percent to about 90.0 percent, by weight.

The compounds of the present invention are effective on many different insects and on acarids. The compounds are effective control agents for insects such as mosquitoes, flies, aphids, weevils and acarids such as the spider mite and ticks. Depending upon the particular combination of the substituents of formula (A) herein, the compounds have a broad or relatively narrow spectrum of unusually high pesticidal activity on insects and acarids. Among the pests against which the compounds of the present invention are pesticidally effective are insects of the order Lepidoptera, Orthoptera, Heteroptera, Homoptera, Diptera, Coleoptera or Hymenoptera, and acarids of the order Acarina including mites of the family Tetranychidae or Tarsonemidae and ticks such as Ornithodoros.

The compounds of the present invention can be used in combination with other pesticides such as the carbamates, phosphates and insect growth regulators, e.g. propoxur, carbaryl, naled, dichlorvos, methoprene, kinoprene, hydroprene, cyhexatin and resmethrin.

The compounds of the present invention of formula (IV) have plant growth regulating activity. They are useful also as intermediates in the synthesis of the corresponding acids, which acids are utilized as starting materials for synthetic pyrethroids. For example, an imidate of formula IV on treatment with an acid, e.g. sulfuric acid, generally at above room temperature, affords the acid corresponding to the imidate (IV) which is then reacted with m-phenoxybenzyl alcohol or the like to form the desired synthetic pyrethroid such as permethrin, fenvalerate, fluvalinate and the like.

The following examples are provided to illustrate the practice of the present invention. Temperature is given in degrees Centigrade. RT means room temperature.

EXAMPLE 1

To a solution of 4.25 g (20 mmol) of 2-(4-chlorophenyl)-3-methylbutanoic acid in 30 ml of ether containing one drop of N,N-dimethylformamide is added dropwise 3.81 g (30 mmol) of oxalyl chloride. The solution is stirred at RT until gas evolution ceases. The solvent and excess oxalyl chloride are removed in vacuo and the residue is taken up in 30 ml of ether. This solution is then added dropwise at 0°–5° to 4.86 g (40 mmol) of a 14% w/w aqueous solution of ammonia. After stirring the mixture for 30 minutes at 0°–5°, the aqueous layer is removed. The ethereal solution is washed with water, dried over sodium sulfate, filtered and concentrated in vacuo to obtain 2-(4-chlorophenyl)-3-methylbutyramide.

To a refluxing solution of 2.72 g (12.9 mmol) of 2-(4-chlorophenyl)-3-methylbutyramide and 2.27 g (8.6 mmol) of 3-phenoxybenzyl bromide in a solution of 15 ml dichloromethane and 3ml ethyl ether is added a solution of 1.83 g (9.5 mmol) of silver tetrafluoroborate in ether. The mixture is refluxed for 2 hours and then separated by pouring into ice cold aqueous ethyl acetate/sodium bicarbonate. The organic phase is washed with water, dried and stripped of solvent. The residue is triturated with ether and filtered. The filtrate is concentrated and chromatographed on silica gel, eluting with 25% ethyl acetate/hexane, and then on plates using 35% ethyl acetate/hexane, to yield 3-phenoxybenzyl 2-(4-chlorophenyl)-3-methylbutanimidate, MS m/e 393 ($M^+$).

EXAMPLE 2

Following the methods of Example 1, 2-(4-chlorophenyl)-3-methylbutanoic acid is reacted with oxalyl chloride and aqueous methylamine to give N-methyl-2-(4-chlorophenyl)-3-methylbutyramide, which is then combined with 3-phenoxybenzyl bromide and $AgBF_4$, yielding 3-phenoxybenzyl N-methyl-2-(4-chlorophenyl)-3-methylbutanimidate, MS m/e 407 ($M^+$).

EXAMPLE 3

Using Example 1 procedures, each of the amides of column I, made by reaction of the corresponding carboxylic acid with ammonia and oxalyl chloride, is reacted with 3-phenoxybenzyl bromide to yield the imidate of column II.

I 2-(4-trifluoromethylphenyl)-3-methylbutyramide
2-(4-fluorophenyl)-3-methylbutyramide
2-phenyl-3-methylbutyramide
2-[4-(difluoromethoxy)pheny]-3-methylbutyramide

II 3-phenoxybenzyl 2-(4-trifluoromethylphenyl)-3-methylbutanimidate
3-phenoxybenzyl 2-(4-fluorophenyl)-3-methylbutanimidate
3-phenoxybenzyl 2-phenyl-3-methylbutanimidate
3-phenoxybenzyl 2-[4-(difluoromethoxy)phenyl]-3-methylbutanimidate

EXAMPLE 4

The compound 2-(4-chlorophenyl)-3-methylbutanoic acid is reacted, as in Example 1, with oxalyl chloride and each of aqueous ethylamine, aqueous aniline and aqueous 4-chloroaniline to give, respectively, N-ethyl-2-(4-chlorophenyl)-3-methylbutyramide, N-phenyl-2-(4-chlorophenyl)-3-methylbutyramide, and N-(4-chlorophenyl)-2-(4-chlorophenyl)-3-methylbutyramide.

Each of the above amides is reacted with 3-phenoxybenzyl bromide and AgBF$_4$, yielding 3-phenoxybenzyl N-ethyl-2-(4-chlorophenyl)-3-methylbutanimidate, N-phenyl-2-(4-chlorophenyl)-3-methylbutanimidate and N-(4-chlorophenyl)-2-(4-chlorophenyl)-3-methylbutanimidate, respectively

EXAMPLE 5

Following the method of Example 1, 3-(2,2-dichloroethenyl)-2,2-dimethylcyclopropaneamide, from 3-(2,2-dichloroethenyl)-2,2-dimethylcyclopropanecarboxylic acid, oxalyl chloride and ammonia, is reacted with 3-phenoxybenzyl bromide to give 3-phenoxybenzyl 3-(2,2-dichloroethenyl)-2,2-dimethylcyclopropanimidate.

EXAMPLE 6

A. A solution of 3.86 g (20 mmol) of 2-(4-chlorophenylamino)-3-methylbutyronitrile in 10 ml of methanol is saturated at reflux with hydrogen chloride gas. When all of the starting nitrile has been consumed, most of the methanol and excess hydrogen chloride is removed in vacuo. Ether is added to precipitate the hydrochloride of methyl 2-(4-chlorophenyl)-3-methylbutanimidate, which is isolated by filtration under nitrogen. The white solid is added with vigorous stirring to an ice-cold mixture of ether and aqueous sodium bicarbonate. The aqueous layer is discarded, and the ethereal layer is washed with cold water and dried over sodium sulfate. Filtration and concentration in vacuo gives methyl 2-(4-chlorophenylamino)-3-methylbutanimidate.

B. A solution of 2.25 g (10 mmol) of methyl 2-(4-chlorophenylamino)-3-methylbutanimidate and 4.00 g (20 mmol) of 3-phenoxybenzyl alcohol is heated with continuous removal of methanol. Upon cessation of methanol evolution, there is obtained an oil, 3-phenoxybenzyl 2-(4-chlorophenylamino)-3-methylbutanimidate.

EXAMPLE 7

Following the procedure described in Example 6, 2-(2-chloro-4-trifluoromethylphenylamino)-3-methylbutyronitrile is reacted with methanol and hydrogen chloride to give methyl 2-(2-chloro-4-trifluoromethylphenylamino)-3-methylbutanimidate, which is then reacted with 3-phenoxybenzyl alcohol, yielding the desired compound 3-phenoxybenzyl 2-(2-chloro-4-trifluoromethylphenylamino)-3-methylbutanimidate.

In like manner, each of the imidates of column III, made from the corresponding nitrile, methanol and HCl, is reacted with 3-phenoxybenzyl alcohol to give the esters of column IV.

III methyl 2-phenylamino-3-methylbutanimidate
methyl 2-(2-fluoro-4-trifluoromethylphenylamino)-3-methylbutanimidate
methyl 2-(2,3,4,5-tetrafluorophenylamino)-3-methylbutanimidate
methyl 2-(4-chloro-2-fluorophenylamino)-3-methylbutanimidate
methyl 2-(6-chloro-2-fluoro-4-trifluoromethylphenylamino)-3-methylbutanimidate

IV 3-phenoxybenzyl 2-phenylamino-3-methylbutanimidate
3-phenoxybenzyl 2-(2-fluoro-4-trifluoromethylphenylamino)-3-methylbutanimidate
3-phenoxybenzyl 2-(2,3,4,5-tetrafluorophenylamino)-3-methylbutanimidate
3-phenoxybenzyl 2-(4-chloro-2-fluorophenylamino)-3-methylbutanimidate
3-phenoxybenzyl 2-(6-chloro-2-fluoro-4-trifluoromethylphenylamino)-3-methylbutanimidate

EXAMPLE 8

A. To a mixture of 2.32 g (11 mmol) of 2-(4-chlorophenyl)-3-methylbutyramide in methylene chloride is added, at room temperature, 1.78 g (12 mmol) of trimethyloxonium tetrafluoroborate. After stirring overnight under nitrogen, the resulting solution is poured onto an ice-cold mixture of ether and aqueous sodium bicarbonate. The aqueous layer is discarded, and the ethereal layer is washed with cold water and dried over sodium sulfate. Filtration and concentration in vacuo affords methyl 2-(4-chlorophenyl)-3-methylbutanimidate.

Following the procedure of Example 6B, 3-phenoxybenzyl alcohol and methyl 2-(4-chlorophenyl)-3-methylbutanimidate are reacted to yield 3-phenoxybenzyl 2-(4-chlorophenyl)-3-methylbutanimidate.

B. In like manner, each of 2-(2-chloro-4-trifluoromethylphenyl)-3-methylbutyramide and 3-(1,2-dibromo-2,2-dichloroethyl)-2,2-dimethylcyclopropaneamide is reacted with trimethyloxonium tetrafluoroborate, giving methyl 2-(2-chloro-4-trifluoromethylphenyl)-3-methylbutanimidate and methyl 2-(1,2-dibromo-2,2-dichloroethyl)-2,2-dimethylcyclopropanimidate, respectively. Each of these imidates is then reacted with 3-phenoxybenzyl alcohol to yield, respectively, 3-phenoxybenzyl 2-(2-chloro-4-trifluoromethylphenyl)-3-methylbutanimidate and 3-phenoxybenzyl 2-(1,2-dibromo-2,2-dichloroethyl)-2,2-dimethylcyclopropanimidate.

EXAMPLE 9

Each of the compounds under column V is reacted with (6-phenoxy-2-pyridyl)methyl alcohol, using the method described in Example 6B, to give the corresponding ester under column VI.

V methyl 2-(4-chlorophenyl)-3-methylbutanimidate
methyl 2-(2-chloro-4-trifluoromethylphenylamino)-3-methylbutanimidate
methyl 2-(2,2-dichloroethenyl)-2,2-dicyclopropanimidate
methyl 2-(1,2-dibromo-2,2-dichloroethyl)-2,2-dicyclopropanimidate

VI (6-phenoxy-2-pyridyl)methyl 2-(4-chlorophenyl)-3-methylbutanimidate
(6-phenoxy-2-pyridyl)methyl 2-(2-chloro-4-trifluoromethylphenylamino)-3-methylbutanimidate
(6-phenoxy-2-pyridyl(methyl 2-(2,2-dichloroethenyl)-2,2-dicyclopropanimidate
(6-phenoxy-2-pyridyl)methyl 2-(1,2-dibromo-2,2-dichloroethyl)-2,2-dicyclopropanimidate Two groups of 10 each 0-24 hour III instar *Heliothis virescens* larvae were treated with 1 μl of the compound 3-phenoxybenzyl 2-(4-chlorophenyl)-3-methylbutanimidate, in acetone at five different concentrations by application to the dorsum of the thorax. Two groups of 10 each are treated identically with 1 μl acetone only as controls. Larvae are held individually in 30 ml plastic cups provided with artificial medium for 72 hours at 25° and 16 hr photoperiod. After 72 hours the number of dead is calculated as a percentage of the total number originally treated and then corrected for any mortality in the control groups using Abbott's formula. The $LD_{50}$ of the compound was less than 0.5%.

The nitrile (V) can be prepared as described in co-pending application Ser. No. 089,003, filed Oct. 29, 1979, now U.S. Pat. No. 4,226,802 the disclosure of which is incorporated by reference.

What is claimed is:

1. A compound of the following formula:

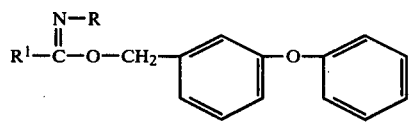 (A)

wherein,

R is hydrogen, lower alkyl, phenyl, or substituted phenyl wherein phenyl is substituted at one, two, or three of the ring carbon atoms with a group selected from lower alkoxy, lower alkyl, lower fluoroalkyl, lower alkenyl, lower haloalkenyl, lower alkenyloxy, halogen, nitro, cyano, and lower alkylthio; and $R^1$ is 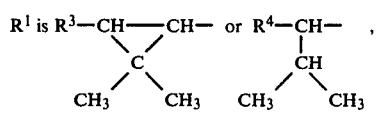

where $R^3$ is lower alkyl, lower haloalkyl, lower alkenyl or lower haloalkenyl; and $R^4$ is the group

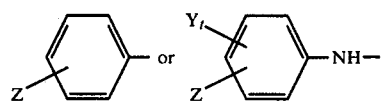

in which t is zero, one, two, three or four; Y is independently selected from hydrogen, lower alkyl, lower fluoroalkyl, lower alkoxy, lower alkylthio, lower alkylcarbonyl, lower alkoxycarbonyl, halogen, and lower fluoroalkylthio; and Z is independently selected from the values of Y, cycloalkyl, and lower fluoroalkoxy.

2. A compound of the following formula, according to claim 1:

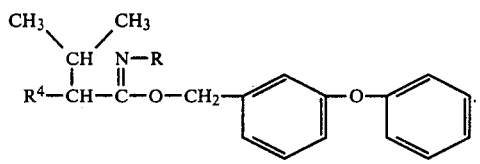

3. A compound of the following formula, according to claim 1:

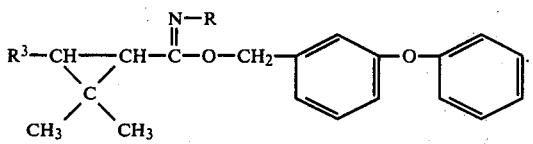

4. The compound according to claim 2 wherein $R^4$ is

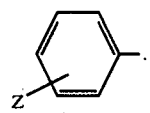

5. The compound according to claim 4 wherein Z is chloro, fluoro, trifluoromethyl or difluoromethoxy and Z is in the para position.

6. The compound according to claim 5 wherein R is hydrogen or methyl.

7. The compound according to claim 5 wherein R is hydrogen.

8. The compound according to claim 2 wherein $R^4$ is

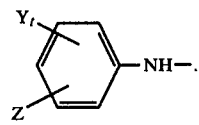

9. The compound according to claim 8 wherein t is zero or one; Y is chloro or fluoro, and is in the ortho position; and Z is chloro, fluoro or trifluoromethyl and is in the para position.

10. The compound according to claim 9 wherein R is hydrogen or methyl.

11. The compound according to claim 9 wherein R is hydrogen.

12. The compound according to claim 3 wherein $R^3$ is 2,2-dichloroethenyl.

13. The compound according to claim 12 wherein R is hydrogen.

14. The compound according to claim 3 wherein $R^3$ is 1,2-dibromo-2,2-dichloroethyl.

15. The compound according to claim 14 wherein R is hydrogen.

* * * * *